United States Patent
Andreas et al.

(10) Patent No.: US 7,192,440 B2
(45) Date of Patent: Mar. 20, 2007

(54) IMPLANTABLE STENT DELIVERY DEVICES AND METHODS

(75) Inventors: Bernard Andreas, Redwood City, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 498 days.

(21) Appl. No.: 10/687,532

(22) Filed: Oct. 15, 2003

(65) Prior Publication Data

US 2005/0085888 A1    Apr. 21, 2005

(51) Int. Cl.
*A61F 2/06* (2006.01)

(52) U.S. Cl. .................... 623/1.11; 623/1.16

(58) Field of Classification Search .......... 623/1.11, 623/903, 1.12, 1.16; 606/108
See application file for complete search history.

(56) References Cited

U.S. PATENT DOCUMENTS

| | | | | |
|---|---|---|---|---|
| 5,104,404 | A * | 4/1992 | Wolff | 623/1.16 |
| 5,282,824 | A * | 2/1994 | Gianturco | 623/1.13 |
| 5,571,086 | A | 11/1996 | Kaplan et al. | |
| 5,662,675 | A * | 9/1997 | Polanskyj Stockert et al. | 606/194 |
| 5,697,948 | A | 12/1997 | Marin et al. | |
| 5,709,701 | A * | 1/1998 | Parodi | 606/194 |
| 5,755,781 | A * | 5/1998 | Jayaraman | 623/1.16 |
| 5,776,141 | A | 7/1998 | Klein et al. | |
| 5,807,398 | A * | 9/1998 | Shaknovich | 623/1.11 |
| 6,090,136 | A * | 7/2000 | McDonald et al. | 623/1.23 |
| 6,123,712 | A * | 9/2000 | Di Caprio et al. | 606/108 |
| 6,123,723 | A * | 9/2000 | Konya et al. | 623/1.11 |
| 6,129,756 | A * | 10/2000 | Kugler et al. | 623/1.27 |
| 6,143,016 | A * | 11/2000 | Bleam et al. | 606/198 |
| 6,258,117 | B1 * | 7/2001 | Camrud et al. | 623/1.16 |
| 6,267,783 | B1 * | 7/2001 | Letendre et al. | 623/1.13 |
| 6,325,823 | B1 * | 12/2001 | Horzewski et al. | 623/1.16 |
| 6,485,510 | B1 | 11/2002 | Camrud et al. | |
| 2002/0037358 | A1 * | 3/2002 | Barry et al. | 427/2.1 |
| 2002/0156496 | A1 * | 10/2002 | Chermoni | 606/194 |
| 2003/0114919 | A1 | 6/2003 | McQuiston et al. | |
| 2003/0135266 | A1 * | 7/2003 | Chew et al. | 623/1.16 |
| 2003/0139797 | A1 | 7/2003 | Johnson et al. | |
| 2003/0225446 | A1 * | 12/2003 | Hartley | 623/1.11 |
| 2004/0093061 | A1 * | 5/2004 | Acosta et al. | 623/1.11 |
| 2004/0215312 | A1 * | 10/2004 | Andreas | 623/1.11 |
| 2005/0288763 | A1 * | 12/2005 | Andreas et al. | 623/1.11 |

* cited by examiner

*Primary Examiner*—Anhtuan T. Nguyen
*Assistant Examiner*—Elizabeth Houston
(74) *Attorney, Agent, or Firm*—Townsend and Townsend and Crew LLP; Jeffry J. Grainger, Esq.

(57) ABSTRACT

Stent delivery devices include at least one implantable stent carrier and/or membrane for carrying multiple stents or stent segments over an expandable member. At least a portion of the implantable carrier is expandable by the expandable member to deploy the portion of the carrier and one or more stent segments disposed thereon. A sheath may be retracted to expose and expand a distal portion of the expandable member to expand and deploy a distal portion of the carrier and the stent segment(s) disposed thereon. Stent delivery devices and methods provide enhanced delivery of multiple stents or stent segments by delivering the segments while coupled with one or more implantable carriers and/or membranes that are typically flexible and dividable.

46 Claims, 4 Drawing Sheets

IMPLANTABLE STENT DELIVERY DEVICES AND METHODS

BACKGROUND OF THE INVENTION

1. Field of the Invention

The present invention relates generally to medical devices and methods. More particularly, the invention relates to apparatus and methods for independently delivering segmented stents or stent grafts within a body lumen.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. In recent years, however, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters, typically inserted through a femoral artery. For self-expanding stents, the stent is simply released from the delivery catheter, and it resiliently expands into engagement with the vessel wall. For balloon expandable stents, a balloon on the delivery catheter is expanded which expands and deforms the stent to the desired diameter, whereupon the balloon is deflated and removed.

Despite many recent advances in stent delivery technology, a number of shortcomings still exist. For example, current stent delivery catheters are not capable of customizing the length of the stent in situ to match the size of the lesion to be treated. While lesion size may be measured prior to stenting, using angiography or fluoroscopy, such measurements may be inexact. If a stent is introduced that is found to be of inappropriate size, the delivery catheter and stent must be removed from the patient and replaced with a different device of correct size. Moreover, current stent delivery devices cannot treat multiple lesions with a single catheter. If multiple lesions are to be treated, a new catheter and stent must be introduced for each lesion to be treated.

Additionally, currently available stent delivery devices are not well-adapted for treating vascular lesions that are very long and/or in curved regions of a vessel. Current stents have a discrete length that is relatively short due to their stiffness. If such stents were made longer, to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents. Such shortcomings in the prior art are addressed by the inventions described in U.S. patent application Ser. No. 10/412,714, entitled "Apparatus and Methods for Delivery of Multiple Distributed Stents," filed on Apr. 10, 2003; and U.S. patent application Ser. No. 10/637,713, entitled "Apparatus and Methods for Delivery of Multiple Distributed Stents," filed on Aug. 8, 2003; both applications assigned to the assignee of the present invention, and both applications being hereby incorporated fully by reference.

Even with improvements such as those described in the above-referenced patent applications, further improvements in stent delivery devices and methods are still being sought. For example, flexibility of a stent is important in stenting long lesions, tortuous vessels, lesions at vessel branches and the like. The above referenced patent applications disclose the use of segmented stents with separate or separable segments to provide highly flexible stents of selectable length. However, in some cases it may be advantageous to use segments that are coupled together during deployment to maintain segment alignment and prevent mobilization of the segments. It may also be beneficial to use interconnected stents to form a tubular passage, such as a graft.

As another example, many balloon-expandable stents are currently delivered by devices in which the stents are in direct contact with the balloon or other expandable member. If such stents are pushed or otherwise advanced along the expandable member in its deflated state, the direct contact between the stents and the balloon during advancement may cause damage to the balloon and/or to the stents or their coatings. A balloon or other expandable member may also interfere with stent advancement, especially after the balloon has been inflated and deflated multiple times and, thus, becomes somewhat flaccid and/or deformed. Thus, stent delivery devices in which the stents directly contact the expandable member may lead to increased risk of balloon or stent damage, increased general wear and tear, difficult stent advancement along the delivery device, and less precise stent placement.

Therefore, a need exists for improved stent delivery devices and methods. Ideally, such devices and methods would provide flexible coupling of stent segments during deployment of the segments. Also ideally, such devices and methods would at least reduce direct contact between stents and the expandable member of the delivery device to reduce damage to the stents and expandable member and to facilitate stent placement. At least some of these objectives will be met by the present invention.

2. Description of the Background Art

U.S. patent application Ser. Nos. 10/412,714 and 10/637,713, previously incorporated by reference, describe apparatus and methods for delivery of multiple distributed stents. U.S. Pat. Nos. 6,485,510 and 6,258,117 to Camrud et al. describe segmented stents with breakable connections between the segments. U.S. Patent Application Publication No. 2002/0156496 (inventor Chermoni) describes a catheter for carrying stents including a stent positioner. U.S. Pat. No. 6,143,016 to Beam et al. describes a stent delivery sheath. U.S. Pat. No. 5,807,398 to Shaknovich describes a shuttle stent delivery catheter. U.S. Pat. No. 5,571,086 (Kaplan et al.) and U.S. Pat. No. 5,776,141 (Klein et al.) describe an expandable sleeve for placement over a balloon catheter for the delivery of one or two stent structures to the vasculature. U.S. Pat. No. 5,697,948 to Marin et al. describes a catheter for delivering stents covered by a sheath. Patent application serial numbers 2003/0139797 (Johnson) and 2003/0114919 (McQuiston) describe covered segmented stents.

BRIEF SUMMARY OF THE INVENTION

Stent delivery devices and methods of the present invention provide for delivering a plurality of stents, a segmented stent or stent grafts in body lumens. Generally, devices of the invention include a stent delivery catheter having at least one implantable carrier and/or membrane for carrying segmented stents. The carrier or membrane allows multiple segments of a stent to be coupled together flexibly during deployment. In some embodiments, the carrier or membrane helps prevent damage to stent segments or to an expandable member caused by contact between the segments and the member. In some embodiments, stent segments and the carrier(s) and/or membrane(s) are deployed from the catheter by retracting a sheath to expose and expand an expandable balloon. The exposed, expanded balloon expands a portion of the implantable carrier or membrane and one or more stent segments disposed thereon, thus deploying the carrier and the segments. In some embodiments, the sheath may subsequently be drawn proximally to further expose and expand the balloon, thus deploying additional portion(s) of the carrier and one or more additional stent segments disposed thereon.

Various embodiments of the invention may be configured to individually and/or selectively deliver multiple stents, multiple stent segments of one stent, multiple stent grafts or stent graft segments, or the like. Although the following description often refers to delivery of "stent segments," this phrase should not be interpreted to limit the scope of the invention in any way. Generally, devices and methods of the invention may be used to delivery any suitable luminal prosthesis, multiple prostheses, or multiple prosthesis segments to a body lumen, and are thus not limited to delivery of one stent, segmented stents or the like.

In one aspect of the present invention, a stent delivery device for delivering a plurality of stents or stent segments to a treatment site comprises: a catheter shaft having a proximal end and a distal end; an expandable member coupled with the catheter shaft near the distal end; at least one implantable carrier disposed over the expandable member; a plurality of stent segments disposed along the carrier; and a sheath slidably disposed over the implantable carrier to constrain expansion of a proximal portion of the expandable member while allowing expansion of a distal portion of the expandable member. The expanded distal portion of the expandable member expands a distal portion of the implantable carrier and at least one stent segment disposed thereon to deliver the distal portion of the implantable carrier and the at least one stent segment.

In some embodiments, the implantable carrier is slidably disposed over the expandable member, while in other embodiments, the carrier may have a fixed position. In slidable embodiments, the catheter device may further include a carrier shaft coupled with the implantable carrier and disposed over the catheter shaft proximal to the implantable carrier for advancing the carrier distally.

Optionally, the sheath may further include at least one carrier cutting member disposed to cut the implantable carrier at one or more locations between the stent segments. For example, the carrier cutting member may comprise a sharpened edge disposed circumferentially about an inner surface of the sheath at a distal end of the sheath. Such embodiments may also include a protective member disposed between the sharpened edge and the expandable member to prevent damage to the expandable member by the sharpened edge. In some embodiments, the carrier cutting member may act as a valve member to provide control of a number of stents segments delivered by the device. Also in some embodiments, expanding the expanding member may press the implantable carrier against the carrier cutting member to divide the distal portion of the carrier from a proximal portion of the carrier.

In some embodiments, the implantable carrier includes at least one dividable connection between at least the distal portion of the carrier and a proximal portion of the carrier. In fact, some embodiments may include multiple dividable connections between multiple carrier portions. Such dividable connections may comprise, for example, perforations, frangible connections, an area of material along the carrier that is thinner than immediately adjacent areas of material, and/or the like. Such connections may be configured to separate or break upon expansion of the expandable member, with or without the use of a cutting member on the sheath. Some of such connection may remain intact following deployment and may remain permanently connected, or may degrade and separate over time.

The carrier itself may be made of any suitable material or combination of materials, such as but not limited to polymers, metals, metal alloys, woven polyesters, polytetrafluoroethylene, ceramics, human tissues, animal tissues and/or the like. In some embodiments, the implantable carrier may include at least one biodegradable or bioresorbable material, or may be made wholly of biodegradable or bioresorbable materials. Also in some embodiments, the implantable carrier may include at least one pharmacological or biological agent, such as but not limited to Rapamycin, Paclitaxel, Rapamycin or Paclitaxel analogs, prodrugs, or derivatives, Everolimus and derivatives thereof, antibiotics, thrombolytics, anti-thrombotics, anti-inflammatories, cytotoxic agents, anti-proliferative agents, vasodilators, gene therapy agents, radioactive agents, immunosuppressants, chemotherapeutics, stem cells and/or the like. In some embodiments, the implantable carrier is non-porous so as to act as a vascular graft, while in other embodiments the carrier is partially or completely porous. In various embodiments, the implantable carrier may comprise a solid tubular wall, a tubular mesh, a tubular scaffold, a helical coil, multiple axial beams or the like. The stent segments may be either fixedly or slidably disposed along the carrier, according to various embodiments.

In some embodiments, the stent delivery device may further include at least one membrane coupled with at least one of the stent segments. In some embodiments, the membrane comprises a continuous membrane coupled with a plurality of stent segments. Alternatively, a plurality of membranes may be coupled with the stent segments such that each membrane is coupled with one of the stent segments or each membrane is coupled with two or more segments. The membrane may be either impermeable or impermeable and may be made of any suitable material or materials. For example, the membrane may comprise at least one biodegradable or bioresorbable material. The membrane may also include at least one pharmacological or biological agent, such as but not limited to Rapamycin, Paclitaxel, Rapamycin or Paclitaxel analogs, prodrugs, or derivatives, antibiotics, thrombolytics, anti-thrombotics, anti-inflammatories, cytotoxic agents, anti-proliferative agents, vasodilators, gene therapy agents, radioactive agents, immunosuppressants, chemotherapeutics, stem cells and/or the like.

In another aspect of the present invention, a stent delivery device for delivering a plurality of stents or stent segments to a treatment site comprises: a catheter shaft having a proximal end and a distal end; an expandable member coupled with the catheter shaft near the distal end; at least one implantable membrane disposed over the expandable member; a plurality of stent segments disposed along the membrane; and a sheath slidably disposed over the implantable membrane to constrain expansion of a proximal portion of the expandable member while allowing expansion of a distal portion of the expandable member. The expanded distal portion of the expandable member expands a distal portion of the implantable membrane and at least one stent segment disposed thereon to deliver the distal portion of the implantable membrane and the at least one stent segment. The membrane or membranes may have any of the characteristics of the membranes described above.

In yet another aspect of the invention, a method for delivering a stent having a plurality of stent segments to a treatment site involves positioning a distal portion of a stent delivery catheter device at the treatment site, the stent delivery catheter having an implantable carrier and a plurality of stent segments disposed along the carrier, and expanding a distal portion of the implantable carrier and at least one distal stent segment disposed thereon to deploy the distal portion of the carrier and the at least one distal stent segment while constraining a proximal portion of the implantable carrier and at least one proximal stent segment disposed thereon.

In some embodiments, expanding the distal portion of the carrier while constraining the proximal portion comprises moving a sheath proximally to expose an expandable member to allow it to expand against the distal portion of the implantable carrier and the at least one distal stent segment. The method may further include moving the sheath proximally to further expose the expandable member to allow it to expand against an additional portion of the implantable carrier and at least one stent segment disposed thereon. This process may be repeated as many times as desired to deploy additional portions of the carrier and additional stent segments. Optionally, the method may also include advancing the implantable carrier in a distal direction along the catheter device, using a carrier shaft located proximal to the carrier on the catheter device. Also optionally, the method may include cutting the implantable carrier with a cutting member to deploy the distal implantable carrier segment.

Further aspects of the nature and advantages of the invention will become apparent from the detailed description below, in conjunction with the drawings.

DETAILED DESCRIPTION OF THE INVENTION

Stent delivery devices of the present invention generally include at least one implantable stent carrier and/or membrane for carrying multiple stents or stent segments over an expandable member. At least a portion of the implantable carrier is expandable by the expandable balloon to deploy the portion of the carrier and one or more stent segments disposed thereon. A sheath, typically disposed over the carrier but alternatively disposed between the carrier and the expandable member, may be retracted to expose and expand a distal portion of the expandable member to expand and deploy a distal portion of the carrier and stent segment(s) disposed thereon. In various alternative embodiments, the carrier may be either slidably or fixedly disposed over the expandable member. In slidable embodiments, the device may further include a carrier shaft disposed proximally of the carrier for advancing the carrier distally over the expandable member. Stent delivery devices and methods of the invention provide enhanced delivery of multiple stents or stent segments by delivering the segments while connected to an implantable carrier and/or membrane that is typically flexible and dividable to deploy a desired length of carrier and associated number of stent segments.

Various embodiments of the invention may be configured to individually and/or selectively deliver multiple stents, multiple stent segments of one stent, multiple stent grafts or stent graft segments, or the like. Although the following description often refers to delivery of "stent segments," this phrase should not be interpreted to limit the scope of the invention in any way. Generally, devices and methods of the invention may be used to delivery any suitable luminal prosthesis, multiple prostheses, or multiple prosthesis segments to a body lumen, and are thus not limited to delivery of one stent, segmented stents or the like. For example, instead of delivering multiple segments of one segmented stent, devices and methods of the invention may be used to deliver multiple stents. Any other suitable configuration is contemplated.

Figure 1:
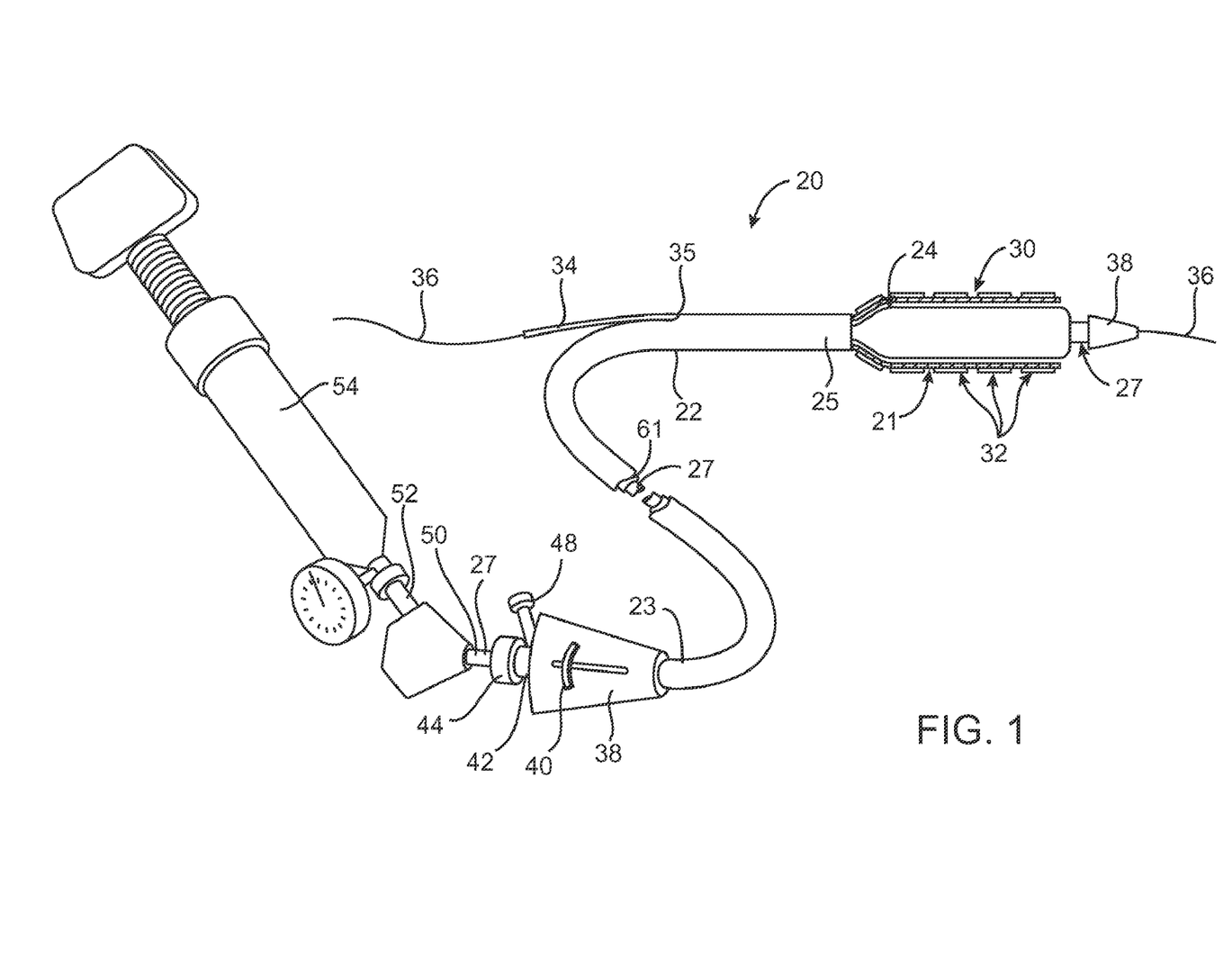
FIG. 1 is a perspective view of a stent delivery catheter according to an embodiment of the invention, with a distal portion of the catheter device shown in cross section with a sheath retracted and an expandable member inflated.

Referring now to FIG. 1, a stent delivery catheter 20 is shown. The catheter 20 is similar to a stent delivery catheter described in U.S. patent application Ser. No. 10/637,713, previously incorporated by reference, but includes an implantable carrier 21 along which a stent 30 having multiple stent segments 32 is disposed. Generally, stent delivery catheter 20 may suitably include a catheter body 22 comprising a sheath 25 slidably disposed over a carrier shaft 61 and an expandable member shaft 27. An expandable member 24, preferably an inflatable balloon (shown in inflated configuration), is mounted to expandable member shaft 27 and is exposed by retracting sheath 25 relative to shaft 27 and expandable member 24. Alternatively, expandable member 24 could be any one of a variety of other mechanically, hydraulically, electrically, or otherwise expandable structures known in the intraluminal catheter arts, such as expandable braids, expandable cages, expandable Mallecott structures, self-expanding structures (including shape memory cages), and the like. A tapered nosecone 28, composed of a soft elastomeric material to reduce trauma to the vessel during advancement of the device, may be mounted distally of expandable member 34.

Stent 30, which preferably comprises a plurality of separate or separable stent segments 32, is disposed on implantable carrier 21, which in turn is disposed on expandable member 24 for expansion therewith, typically being coaxially and slidably received over expandable member shaft 27. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof. Other designs where a guidewire is received through the entire length of shafts 27 and 61 are also contemplated within the present invention.

A handle or hub 38 is mounted to a proximal end 23 of sheath 25 and includes an actuator 40 slidably mounted thereto for purposes described below. An adaptor 42 is mounted to the proximal end of handle 38 and provides a catheter port 44 through which shaft 27 is slidably positioned. A flush port 48 is mounted to the side of adaptor 42 through which a fluid such as saline can be introduced into the interior of catheter body 22. An annular seal (not shown) in catheter port 44 seals around shaft 27 to prevent fluid from leaking through catheter port 44. Optionally, a clamp (not shown) such as a threaded collar, can be mounted to catheter port 44 to lock shaft 27 relative to handle 38. While adaptor 42 is shown separately from handle 38, the structures could be made integral to each other as well.

Expandable member shaft 27 has a proximal end 50 to which is mounted an inflation adaptor 52 (which could also be formed integrally with handle 38). Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen in shaft 27 to enable inflation of expandable member 24. For further description of devices and methods for delivering distributed stents, as well as various embodiments of stents themselves, reference may be made to U.S. patent application Ser. Nos. 10/412,714 and 10/637,713, previously incorporated by reference.

As mentioned above and described in more detail below, the configuration of stent delivery catheter 20 make take any of a number of alternative forms. For example, implantable carrier 21 may be disposed within sheath 25 and around expandable member 24. In an alternative embodiment, implantable carrier 21 may be slidably or fixedly disposed over sheath 25. Implantable carrier 21 may comprise a relatively long tubular member, perhaps extending much or all of the length of catheter 20, or alternatively may be a relatively short tubular member disposed at or near the distal end of catheter 20. Various implantable carriers 21 may be either fixed or slidable relative to expandable member 24, expandable member shaft 27 and/or sheath 25. Slidable embodiments typically include proximal carrier shaft 61, disposed proximal to carrier 21, to advance carrier 21 along expandable member shaft 27 and/or expandable member 24. Stents 30, with stent segments 32, are typically fixedly mounted on implantable carrier 21, but slidable mounting is also contemplated within the invention. Therefore, FIG. 1 depicts only one exemplary embodiment of a stent delivery device and in no way should be interpreted to limit the scope of the invention.

Stent segments 32 are described more fully in U.S. patent application Ser. No. 10/637,713, previously incorporated by reference, and Application Ser. No. 60/440,839, filed Jan. 17, 2003, which is incorporated herein by reference. In an exemplary embodiment, each stent segment is about 2–8 mm in length, and up to 10–50 stent segments may be positioned end-to-end in a line over implantable carrier 21. Stent segments 32 preferably are in direct contact with each other, but may be mounted with suitable spacing between segments to facilitate deployment of each segment without interference with adjacent segments. Alternatively, separate spacing elements may be disposed between adjacent stent segments 32. Such spacing elements may be plastically deformable or self-expanding so as to be deployable with stent segments 32 into the vessel.

Stent segments 32 are preferably a malleable metal so as to be plastically deformable by expandable member 24 as they are expanded to the desired diameter in the vessel. Alternatively, stent segments 32 may be formed of an elastic or super-elastic shape memory material such as Nitinol, so as to self-expand upon release into the vessel by retraction of sheath 25. Stent segments 32 may also be composed of polymers or other suitable biocompatible materials. In self-expanding embodiments, expandable member 24 may also be used for pre-dilatation of a lesion prior to stent deployment or for augmenting the expansion of the self-expanding stent segments. In some embodiments, stent segments 32 are coated with a drug that inhibits restenosis, such as Rapamycin, Paclitaxel, analogs, prodrugs, or derivatives of Rapamycin or Paclitaxel, or other suitable agent(s), preferably carried in a bioerodable polymeric carrier. Alternatively, stent segments 32 may be coated with other types of drugs and therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics, stem cells or the like. Such materials may be coated over all or a portion of the surface of stent segments 32, or stent segments 32 may include apertures, holes, channels, or other features in which such materials may be deposited.

Stent segments 32 may have a variety of configurations, including but not limited to those described in Application Ser. No. 60/440,839, previously incorporated by reference. In some embodiments, stent segments 32 are completely separate from one another without any interconnections, while in alternative embodiments a stent may include couplings between two or more adjacent segments which permit flexion between the segments. As a further alternative, one or more adjacent stent segments 32 may be connected by separable or frangible couplings that are separated prior to or upon deployment, as described in U.S. application Ser. No. 10/306,813, filed Nov. 27, 2002, which is incorporated herein by reference.

Figure 2A:
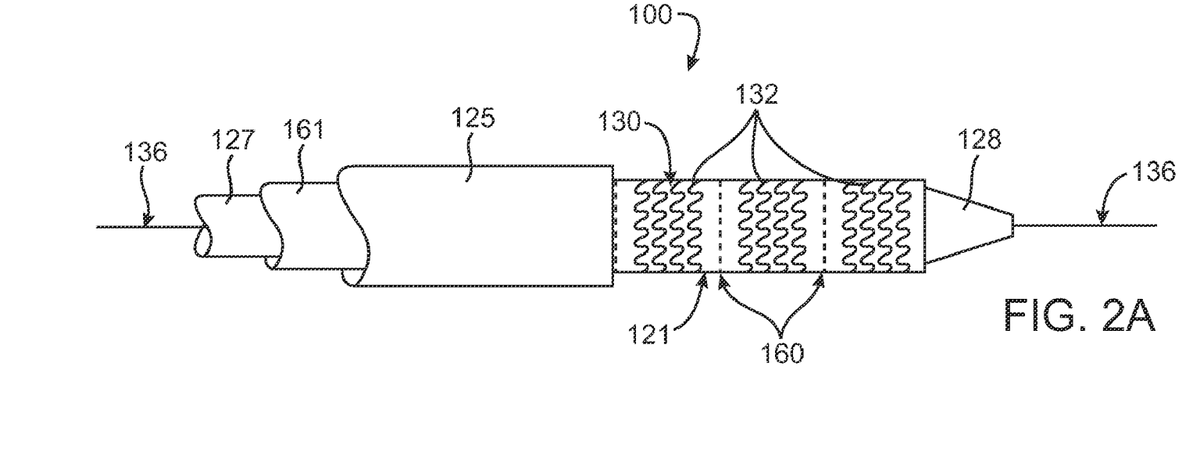
FIG. 2A is a side view of a distal portion of a stent delivery catheter having an implantable, dividable carrier and stent segments, according to one embodiment of the present invention.

Referring now to FIG. 2A, a distal portion of one embodiment of a stent delivery catheter 100 is shown in side view. Stent delivery catheter 100 may suitably include an expandable member shaft 127, a carrier shaft 161 disposed over expandable member shaft 127, a sheath 125 disposed over carrier shaft 161, and a nosecone 128 distally mounted to expandable member shaft 127. Expandable member shaft 127, carrier shaft 161, sheath 125 and nosecone 128 may allow for passage of a guidewire 136. Stent segments 132 may be disposed along an implantable carrier 121 coupled with carrier shaft 127, such that each stent segment 132 is positioned on a portion of carrier 121 that is dividable from adjacent carrier portions via perforations 160. In alternative embodiments, two or more stent segments may be disposed over one dividable carrier portion. Also, as described further below, any suitable means for dividing adjacent carrier portions may be used, with perforations 160 being merely one example. In the pictured embodiment, implantable carrier 121 and stent segments 132 are disposed over an expandable member (not shown) and within sheath 125. Sheath 125 may thus be retracted, as shown, to expose implantable carrier 121, stent segments 132 and the expandable member.

Figure 2B:
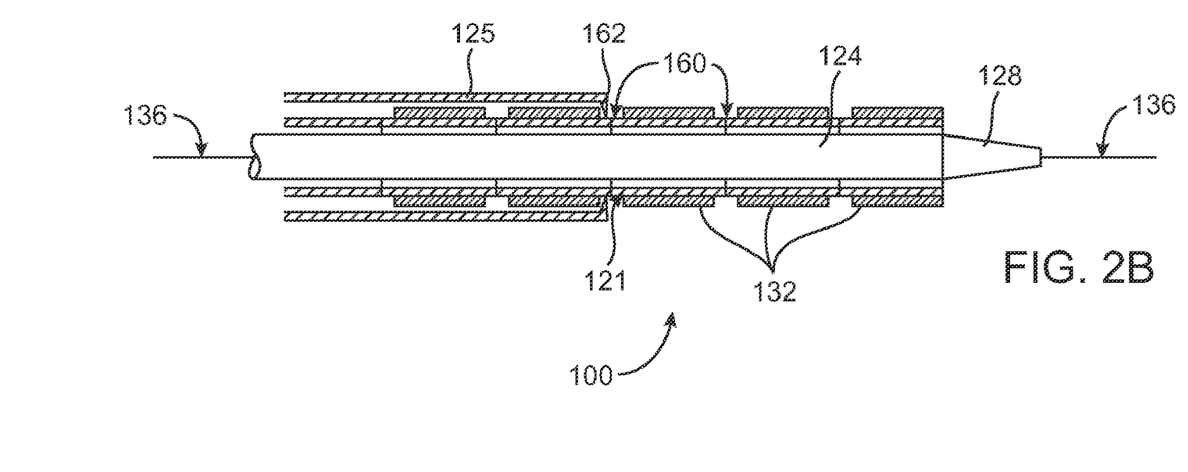
FIG. 2B is a side cross-sectional view of the distal portion of the stent delivery catheter shown in FIG. 2A.

FIG. 2B shows the distal end of stent delivery device 100 in cross-section so that expandable member 124 can be seen within carrier 121, stent segments 132 and sheath 125. Also visible in FIG. 2B is a valve 162 on the distal end of sheath 125. As is described in further detail below, valve 162 may allow for regulation of spacing between of stent segments 132 being exposed from inside sheath 125 and those within sheath 125. Valve 162 may also act as a cutting mechanism for separating adjacent segments of carrier 121.

Although the embodiment in FIGS. 2A and 2B is shown with sheath 125 disposed over carrier 121 and carrier shaft 161, in alternative embodiments a carrier and carrier shaft may be disposed over a sheath. In such embodiments, the sheath serves to contain the expandable member, and when the sheath is retracted, the expandable member expands to deploy the implantable carrier and the stent segment(s). Therefore, although the figures and the following description generally focuses on embodiments in which the sheath covers the carrier and stent segments, the invention is not limited to such embodiments.

That being said, implantable carrier 121 may be composed of any suitable material or combination of materials and may have any suitable length, inner diameter, thickness and other characteristics. Generally, at least part of implantable carrier 121 will be expandable so that expandable member 124 can expand one or more portions of implantable carrier 121 to deploy those portions and their corresponding stent segment(s) 132. Implantable carrier 121 may thus be expandable along its entire length or only along a portion of its length near the distal end. Implantable carrier 121 will also be dividable into carrier portions (or "segments"), such that each portion corresponds to one or more overlying stent segments 132. Carrier portions are coupled with adjacent carrier portions by perforations 160 or connective mechanisms for allowing the segments to be divided from one another. Other connective mechanisms may include, for example, frangible or breakable connections, thinned sections of carrier material and/or the like. Typically, deployable portions of implantable carrier 121 are composed of one or more biocompatible materials, such as a biocompatible polymer, metal, woven polyester, PTFE or anatomical tissue (human or animal). Carrier shaft 161 may be made of any suitable flexible material, such as polyimide, PTFE, FEP, Pebax or any other suitable polymer. To enhance axial sliding over expandable member 124, implantable carrier 121 may be made of a friction-reducing or friction-minimizing material and/or may be covered with a friction reducing coating.

In some embodiments, implantable carrier 121 may be fixedly coupled with delivery catheter 100 so that it does not slide axially relative to expandable member shaft 127, expandable member 124 or the like. In other embodiments, implantable carrier 121 may be slidably coupled with catheter 100 to allow it to move axially relative to one or more catheter components. As mentioned above, implantable carrier 121 and its segments may have any suitable length, configuration and the like. In some embodiments, for example, carrier 121 may be a tubular member disposed near the end of stent delivery device 100, having a length coinciding with the length of stent 130. In another embodiment, carrier 121 may extend the entire (or nearly the entire) length of stent delivery device 100, with a distal portion of carrier 121 being expandable and deployable. In some embodiments, carrier shaft 161 may be a piece coupled with carrier 121, while in other embodiments shaft 161 and carrier 121 may be integral. Still other embodiments may not include a carrier shaft. Thus, many various embodiments are contemplated within the scope of the invention.

In use, sheath 125 is withdrawn proximally to allow a portion of expandable member 124 to expand. Expandable member 124 (shown in unexpanded configuration) then expands to contact, expand and deploy one or more portions of implantable carrier 121 and one or more corresponding stent segments 132. In this way, a selectable length of implantable carrier 121 and stent segments 132 may be expanded and deployed one at a time or in groups. As sheath 125 is withdrawn proximally, more expandable member 124 is exposed, and additional portions of implantable carrier 121 and stent segments 132 are expanded and deployed. In some embodiments, the expansion of expandable member 124 against implantable carrier 121 will generate enough force to separate an expanded, distal carrier portion from an unexpanded, proximal carrier portion at perforations 160 or alternative breakable connections between the portions. In these or other embodiments, it may be advantageous to also have a carrier-cutting valve 162 disposed on sheath 125 to assist or enable separation of carrier segments. Valve 162 may also enhance the ability of a user to control the number and spacing of stent segments 132 that are deployed from delivery device 100. Cutting valve 162 may have any suitable configuration, such as a ring of sharpened, inwardly facing material at or near the distal end of sheath 125, as pictured in FIG. 2B. In another embodiment, portions of carrier 121 may be separated using a heated wire disposed around the distal end of sheath 125 or on cutting valve 162. In any case, cutting valve 162 and/or other carrier cutting members will be configured to separate adjacent carrier portions without cutting or damaging expandable member 124, but some embodiments may further include one or more protective members for protecting expandable member 124 from damage by cutting valve 162.

Stent segments 132 may be coupled with corresponding segments of carrier 121 in any suitable way, such as by adhesive, sutures, staples, clips, fixation features on stent segments 132, crimping stent segments 132 on carrier 121, partial or total encapsulation of stent segments 132 in carrier material, and/or the like. In fact, although stent segments 132 are shown disposed over carrier 121, in other embodiments segments 132 may be disposed beneath or within carrier 121. For example, carrier 121 may be covering the outer surface of segments 132 and may contain an anti-restenosis agent which elutes from carrier 121 into the vessel wall.

In some embodiments, stent segments 132 may be coupled to one or more implantable membranes (not shown) instead of or in addition to carrier 121. In one embodiment, a membrane may comprise one continuous, tubular membrane that extends between all stent segments 132 of stent 130. Alternatively, a membrane may extend between multiple stent segments 132 along only a portion of stent 130. Such a membrane may act as a graft, for example. In still other embodiments, multiple unconnected membranes may be used, with each membrane covering one or more stent segments 132. Furthermore, membrane(s) may be coupled with stent segments 132 in any suitable configuration. For example, membranes may be disposed on an outer surface of stent segments 132, an inner surface, within openings in segments 132, or the like. Membranes may be adhered to the segments 132 via any suitable process, such as coating, dipping, adhesive fixation or the like. The membranes may be permeable, made of a material such as Dacron, PTFE or the like, or impermeable, made of urethane, other elastomers or the like. Some membranes may be biodegradable, bioresprbable or bioerodable, while others remain intact over time. The membranes may also be coated, impregnated or otherwise coupled with one or more pharmaceutical agents such as a drug that inhibits restenosis, such as Rapamycin, Paclitaxel, analogs, prodrugs, or derivatives of Rapamycin or Paclitaxel, or other suitable agent, preferably carried in or coated with a bioerodable polymeric carrier. Alternatively, membranes may be coated with other types of drugs and therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics or stem cells. Such materials may be coated over all or a portion of the surface of a membrane, or the membrane may include apertures, holes, channels, or other features in which such materials may be deposited.

Figure 3A:
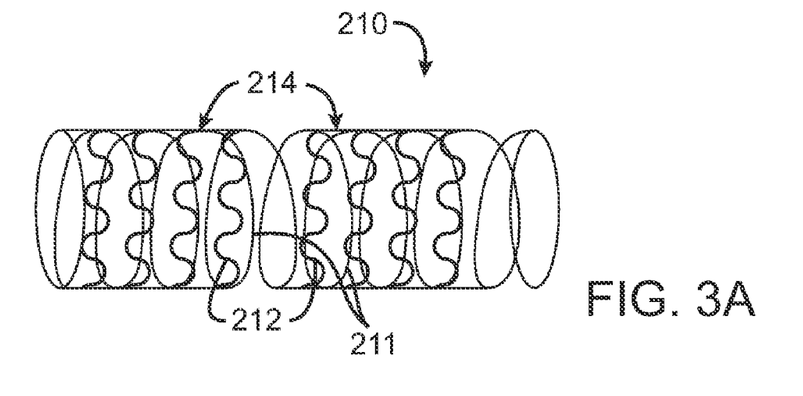
FIGS. 3A–3C are side views of various embodiments of an implantable, dividable stent carrier, according to various embodiments of the present invention.
Figure 3B:
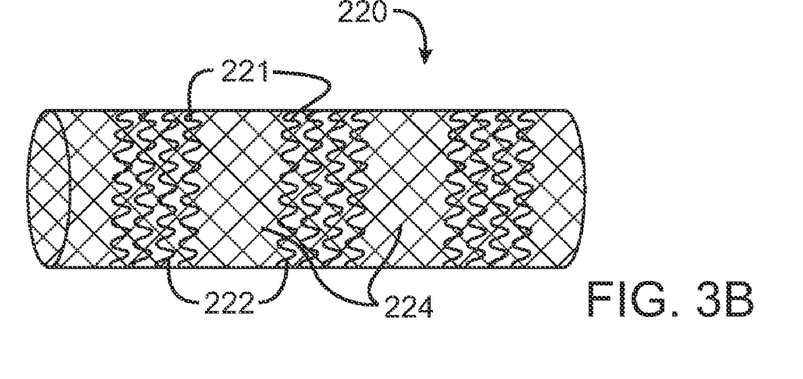
Figure 3C:
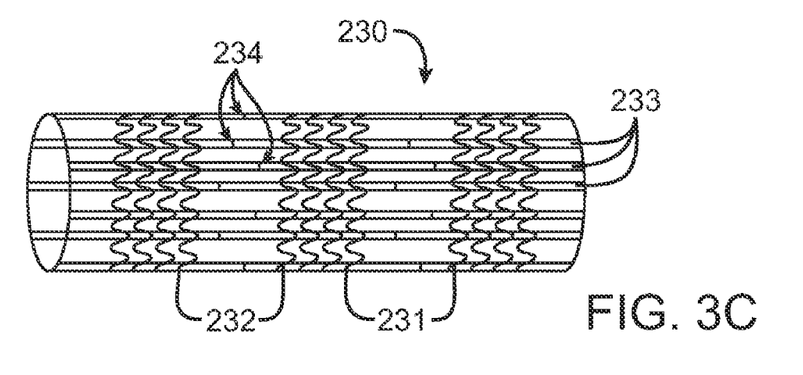

Implantable carriers of the present invention may take any of a number of different forms and are not limited to any specific embodiments described herein. Examples of such embodiments are shown in FIGS. 3A–3C, however it should be emphasized that these are examples only and should not be interpreted to limit the scope of the invention. That being said, FIG. 3A demonstrates one embodiment of an implantable carrier 210 comprising a coil. The coiled carrier 210 includes multiple carrier segments 211 corresponding with overlying stent segments 212. In one embodiment, horizontal struts 214 may be used to strengthen each carrier segment 211, while areas between adjacent segments do not include struts, to allow for division of the segments 211 from each other. Such an embodiment may also include perforations or other frangible, breakable or bioerodable connections between carrier segments 211, to facilitate division between segments 211. In various embodiments, as already discussed, carrier segments 211 may each contain one stent segment 212 or multiple stent segments 212.

In another embodiment, as in FIG. 3B, an implantable carrier 220 may be made of a mesh, scaffold or lattice configured material. In one embodiment, carrier segments 221 may have a tighter-weaved, thicker or otherwise stronger mesh than breakable areas 224 of carrier 220 between segments 221, to allow for division of adjacent carrier segments 221, to deploy the segments 221 and the corresponding stent segments 222. Again, frangible, breakable or bioerodable connections may also, or alternatively, be included between carrier segments 221. Referring to FIG. 3C, another embodiment of an implantable carrier 230 includes multiple axial beams 233, each beam 233 including break points 234 located between carrier segments 231 and their corresponding stent segments 232. These exemplary embodiments demonstrate that implantable carriers, carrier segments and breakable mechanisms may have any number of various configurations.

In any of the above embodiments or in other embodiments, an implantable carrier may be made of one or more biodegradable, bioresorbable or bioerodable materials, such that the carrier will eventually dissolve or degrade to leave only the unconnected stent segments in the vessel or other body lumen. Such embodiments thus enhance delivery of the stent segments, by providing a flexible carrier for supporting the segments, while leaving no permanent additional material in the vessel other than the stent segments. In other embodiments, of course, the implantable carrier may be may of non-degradable material(s), so as to remain in the vessel over a longer period. Such may be advantageous, for example, if the carrier-stent structure is to function as a vascular graft. In various embodiments, carriers may also elute one or more therapeutic agents and/or may dissolve or degrade to distribute such agent(s).

Figure 4A:
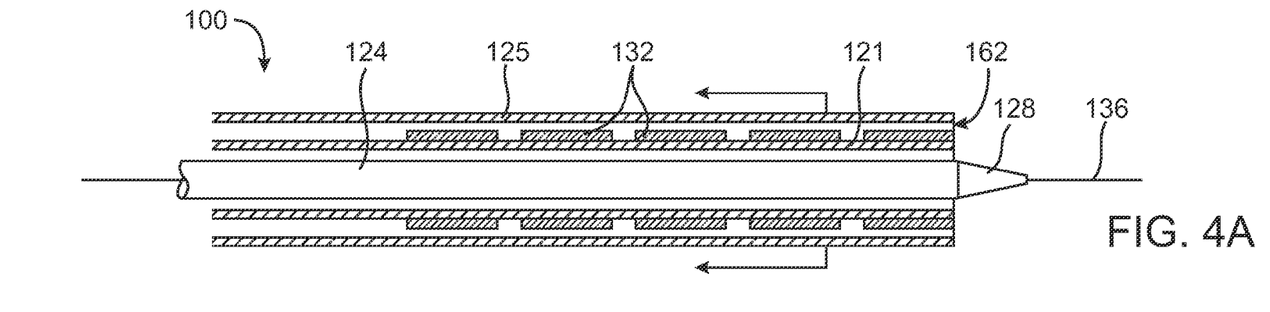
FIG. 4A–4C demonstrate a method for delivering a plurality of stent segments and an implantable carrier segment at a treatment site, according to one embodiment of the invention.
Figure 4B:
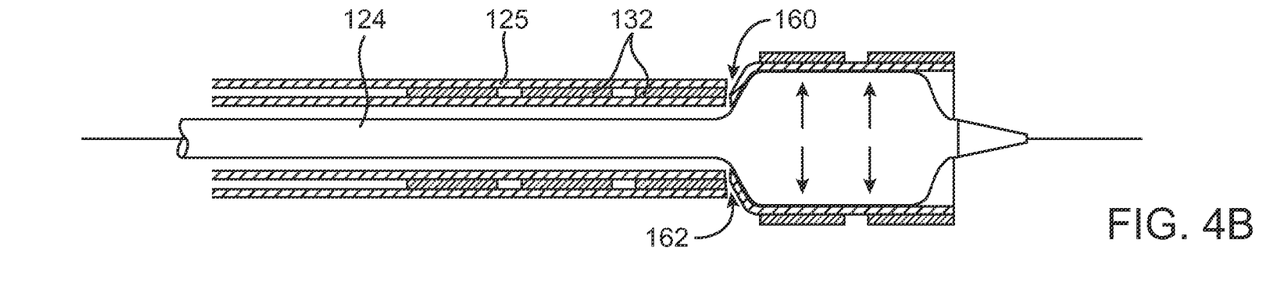
Figure 4C:
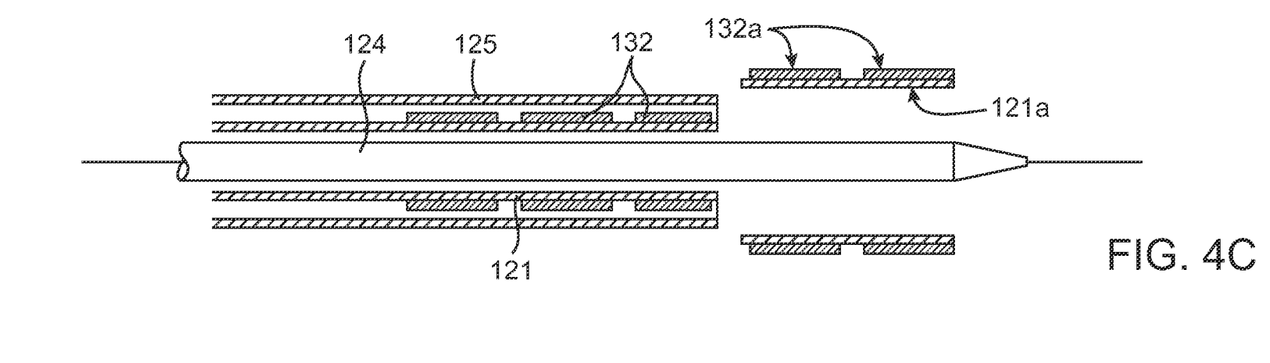

Referring now to FIGS. 4A–4C, a method for delivering stent segments is shown. (For purposes of clarity no vasculature or other lumen is shown.) Generally, a stent delivery catheter 100 will be advanced through a patient's vasculature or other lumen to a desired location for delivering stent segments 132 and corresponding segments of implantable carrier 121. At that point, sheath 125 may be withdrawn or retracted proximally, as shown by the two proximally directed arrows in FIG. 4A, to expose at least part of expandable member 124 within carrier 121. Exposed expandable member 124 may then be expanded, or may self-expand, as shown in FIG. 4B. Upon such expansion, expandable member 124 contacts and expands an expandable portion of implantable carrier 121, which in turn causes one or more stent segments 132 to expand. Expansion of expandable member 124 also causes division of implantable carrier 121 via perforations 160 or other breakable mechanism, such that a proximal portion of carrier 121 remains within sheath 125 and a distal portion of carrier 121a is deployed with corresponding deployed stent segments 132a, as shown in FIG. 4C. A cutting member 162 may also assist in dividing the proximal portion of carrier 121 from the distal portion 121a. When expandable member 124 is subsequently deflated, deployed implantable carrier 121a and deployed stent segments 132a remain expanded and in place. As mentioned above, deployed implantable carrier 121a may then elute one or more therapeutic agents, biodegrade with in the vessel, and/or the like. A physician may then reposition catheter 100 to another site, retract sheath 125 further proximally and expand expandable member 124 to deploy additional implantable carrier segments and corresponding stent segments 132 of appropriate length. When a procedure is finished, a physician may advance sheath 125 distally to cover expandable member 124. Many variations on the method just described may be used without departing from the scope of the present invention, for example by adding, subtracting or substituting method steps.

Although the above is complete description of the preferred embodiments of the invention, various alternatives, additions, modifications and improvements may be made without departing from the scope thereof, which is defined by the claims.

What is claimed is:

1. A stent delivery device for delivering a plurality of stents or stent segments to a treatment site in a body lumen, the device comprising:

a catheter shaft having a proximal end and a distal end;

an expandable member coupled with the catheter shaft near the distal end;

at least one implantable carrier disposed over the expandable member, the implantable carrier being dividable at a plurality of locations along its length;

a plurality of stent segments disposed along the carrier; and a sheath slidably disposed over the implantable carrier to constrain expansion of a proximal portion of the expandable member while allowing expansion of a distal portion of the expandable member, wherein the sheath is adapted to divide the implantable carrier at one of the locations, wherein a distal portion of the expandable member expands a distal portion of the implantable carrier and at least one stent segment disposed thereon to deploy the distal portion of the implantable carrier and the at least one stent segment in the body lumen while a second portion of the implantable carrier remains unexpanded within the sheath.

2. A device as in claim 1, wherein the implantable carrier is slidably disposed over the expandable member.

3. A device as in claim 2, further including a carrier shaft coupled with the implantable carrier and disposed over the catheter shaft proximal to the implantable carrier for advancing the carrier distally.

4. A device as in claim 1, wherein the sheath further comprises at least one carder cutting member disposed to cut the implantable carrier at one or more locations between the stent segments.

5. A device as in claim 4, wherein the carrier cutting member comprises a sharpened edge disposed circumferentially about an inner surface of the sheath at a distal end of the sheath.

6. A device as in claim 5, further including a protective member disposed between the sharpened edge and the expandable member to prevent damage to the expandable member by the sharpened edge.

7. A device as in claim 4, wherein the carrier ending member acts as a valve member to provide control of a number of stents segments delivered by the device.

8. A device as in claim 4, wherein expanding the expanding member presses the implantable carrier against the carrier cutting member to divide the distal portion of the carrier from a proximal portion of the carrier.

9. A device as in claim 1, wherein the implantable carrier comprises at least one dividable connection between at least the distal portion of the carrier and a proximal portion of the carrier.

10. A device as in claim 9, wherein the at least one dividable connection comprises multiple dividable connections between multiple carrier portions.

11. A device as in claim 9, wherein each of the at least one dividable connections comprises at least one of perforations, frangible connections and an area of material along the carrier that is thinner than immediately adjacent areas of material.

12. A device as in claim 9, wherein the at least one dividable connection is preformed in the carrier.

13. A device as in claim 1, wherein the implantable carrier comprises at least one material selected from the group consisting of a polymer, a metal, a metal alloy, a woven polyester, polytetrafluoroethylene, a ceramic, human tissue and animal tissue.

14. A device as in claim 1, wherein the implantable earner comprises at least one biodegradable or bioresorbable material.

15. A device as in claim 1, wherein the implantable carrier comprises at least one pharmacological or biological agent.

16. A device as in claim 15, wherein the pharmacological agent is selected from the group consisting o Rapamycin. Paclitaxel, Rapamycin or Paclitaxel analogs, Everolimus and derivatives thereof, prodrugs, or derivatives, antibiotics, thrombolytics, anti-thrombotics, anti-inflammatories, cytotoxic agents, anti-proliferative agents, vasodilators, gene therapy agents, radioactive agents, immunosuppressants, chemotherapeurics and stem cells.

17. A device as in claim 1, wherein the implantable carrier is non-porous so as to act as a vascular graft.

18. A device as in claim 1, wherein the implantable carrier comprises a solid tubular wall.

19. A device as in claim 1, wherein the implantable carrier comprises a tubular mesh.

20. A device as in claim 1, wherein the implantable carrier comprises a tubular scaffold.

21. A device as in claim 1, wherein the implantable carrier comprises a helical coil.

22. A device as in claim 1, wherein the implantable carrier comprises multiple axial beams.

23. A device as in claim 1, wherein the plurality of stent segments are fixedly disposed along the carrier.

24. A device as in claim 1, further comprising at least one membrane coupled with at least one of the plurality of stein segments.

25. A device as in claim 24, wherein the at least one membrane is permeable.

26. A device as in claim 24, wherein the at least one membrane is impermeable.

27. A device as in claim 24, wherein the at least one membrane comprises a continuous membrane coupled with the plurality of stent segments.

28. A device as in claim 24, wherein the at least one membrane comprises a plurality of membranes, each membrane coupled with at least one of the plurality of segments.

29. A device as in claim 24, wherein the at least one membrane comprises a plurality of membranes, each membrane coupled with two or more of the plurality of stent segments.

30. A device as in claim 24, wherein the at least one membrane comprises at least one biodegradable or bioresorbable material.

31. A device as in claim 24, wherein the at least one membrane comprises at least one pharmacological or biological agent.

32. A device as in claim 31, wherein the pharmacological agent is selected from the group consisting of Rapamycin, Paclitaxel, Rapamycin or Paclitaxel analogs, prodrugs, or derivatives, antibiotics, thrombolytics, anti-thrombotics, anti-inflammatories, cytotoxic agents, anti-proliferative agents, vasodilators, gene therapy agents, radioactive agents, immunosuppressants, chemotherapeutics and stem cells.

33. A device as in claim 31, wherein Pie pharmacological agent is selected from the group consisting of Rapamycin, Paclitaxel, Rapamycin or Paclitaxel analogs, prodrugs, or derivatives, antibiotics, thrombolytics, anti-thrombotics, anti inflammatories, cytotoxic agents, anti-proliferative agents, vasodilators, gene therapy agents, radioactive agents, immunosuppressants, chemotherapeutics and stem cells.

34. A stent delivery device for delivering a plurality of stents or stent segments to a treatment site in a body lumen, the device comprising:
  a catheter shaft having a proximal end and a distal end;
  an expandable member coupled with the catheter shaft near the distal end;
  at least one implantable membrane disposed over the expandable member, the implantable membrane being dividable at a plurality of locations along its length;
  a plurality of slant segments disposed along the membrane; and
  a sheath slidably disposed over the implantable membrane to constrain expansion of a proximal portion of the expandable member while allowing expansion of a distal portion of the expandable member, wherein the sheath is adapted to divide the implantable membrane at one of the locations,
  wherein a distal portion of the expandable member expands a distal portion of the implantable membrane and at least one stent segment disposed thereon to deploy the distal portion of the implantable membrane and the at least one stent segment in the body lumen while a second portion of the implantable membrane remains unexpanded within the sheath.

35. A device as in claim 34, wherein the at least one membrane is permeable.

36. A device as in claim 34, wherein the at least one membrane is impermeable.

37. A device as in claim 34, wherein the at least one membrane comprises a continuous membrane coupled with a plurality of stent segments.

38. A device as in claim 34, wherein the at least one membrane comprises a plurality of membranes, each membrane coupled with at least one of the plurality of stent segments.

39. A device as in claim 34, wherein the at least one membrane comprises a plurality of membranes, each membrane coupled with two or more of the plurality of stent segments.

40. A device as in claim 34, wherein flue at least one membrane comprises at least one biodegradable or bioresorbable material.

41. A device as in claim 34, wherein the at least one membrane is coupled with at least one pharmacological or biological agent.

42. A method for detivering a stent having a plurality of stem segments to a treatment site in a body lumen, the method comprising;
   positioning a distal portion of a stent delivery catheter device at the treatment site, the stent delivery catheter having an implantable carrier and a plurality of stent segments disposed along the carrier; and
   expanding a distal portion of the implantable carrier and at least one distal stent segment disposed thereon to deploy the distal portion of the carrier and the at least one distal stent segment while constraining a proximal portion of the implantable carrier and at least one proximal stent segment disposed thereon; and
   dividing the implantable carrier between the distal portion and the proximal portion so as to allow deployment of the distal portion of the implantable carrier and the at least one distal stent segment in the body lumen while a second portion of the implantable carrier remains unexpanded within the sheath.

43. A method as in claim 42, wherein expanding the distal portion of the carrier while constraining the proximal portion comprises moving a sheath proximally to expose an expandable member to allow it to expand against the distal portion of the implantable carrier and the at least one distal stent segment.

44. A method as in claim 43, further comprising moving the sheath proximally to further expose the expandable member to allow it to expand against an additional portion of the implantable carrier and at least one steal segment disposed thereon.

45. A method as in claim 42, further comprising advancing the implantable carrier in a distal direction along the catheter device, using a carrier shaft located proximal to the carrier on the catheter device.

46. A method as in claim 42, wherein dividing the implantable carrier comprises cutting the implantable carrier with a cutting member to deploy the distal implantable carrier segment.

* * * * *

UNITED STATES PATENT AND TRADEMARK OFFICE
CERTIFICATE OF CORRECTION

PATENT NO. : 7,192,440 B2
APPLICATION NO. : 10/687532
DATED : March 20, 2007
INVENTOR(S) : Andreas et al.

It is certified that error appears in the above-identified patent and that said Letters Patent is hereby corrected as shown below:

Column 12, line 65, please delete "carder" and insert --carrier--.

Column 13, line 9, please delete "ending" and insert --cutting--.

Column 13, line 35, please delete "earner" and insert --carrier--.

Column 13, line 41, please delete "o Rapamycin." and insert --of Rapamycin,--.

Column 13, line 64, please delete "stein" and insert --stent--.

Column 14, line 28, please delete "Pie" and insert --the--.

Column 14, line 45, please delete "slant" and insert --stent--.

Column 15, line 9, please delete "flue" and insert --the--.

Column 15, line 15, please delete "detivering" and insert --delivering--.

Column 15, line 16, please delete "stem" and insert --stent--.

Column 16, line 16, please delete "steal" and insert --stent--.

Signed and Sealed this

Second Day of October, 2007

JON W. DUDAS
*Director of the United States Patent and Trademark Office*